United States Patent [19]

Chen

[11] Patent Number: 5,208,327
[45] Date of Patent: May 4, 1993

[54] INTERMEDIATES USEFUL IN A SYNTHESIS OF 2-CHLORO-2'-DEOXYADENOSINE
[75] Inventor: Robert H. K. Chen, Belle Mead, N.J.
[73] Assignee: Ortho Pharmaceutical Corporation, Raritan, N.J.
[21] Appl. No.: 869,689
[22] Filed: Apr. 16, 1992

Related U.S. Application Data

[63] Continuation-in-part of Ser. No. 810,992, Dec. 18, 1991, abandoned.
[51] Int. Cl.[5] .................. C07H 19/167; C07H 19/173
[52] U.S. Cl. .................................... 536/27.7; 514/46
[58] Field of Search .................................. 536/24, 26
[56] References Cited

U.S. PATENT DOCUMENTS 4,760,137  7/1988  Robins et al. ......................... 536/26

OTHER PUBLICATIONS

Robins et al., "Smooth and Efficient Degradation of Secondary Alcohols. A General Procedure for the Conversion of Ribonucleosides to 2'-Deoxynucleosides," *J. Am. Chem. Soc.*, 103, 932,933 (1981).
Nair et al.(I), "Modification of Nucleic Acid Bases via Radical Intermediates: Synthesis of Dihalogenated Purine Nucleosides," *Synthesis*, 1982, 670-672.
Barton et al., "A New Method for the Deoxygenation of Secondary Alcohols," *J. Chem. Soc. Perkin I*, 1975, 1574-1585.
Nair et al.(II), "Utility of Purinyl Radicals in the Synthesis of Base-Modified Nucleosides and Alkylpurines: 6-Amino Group Replacement by H, Cl, Br and I," *J. Org. Chem.*, 45(20), 3969-3974 (1980).
Seto et al., "Biochemical Basis for Deoxyadenosine and 2-Chlorodeoxyadenosine Toxicity to Resting Human Lymphocytes," in *Purine and Pyrimidine Metabolism in man V*, Nyhan et al. (eds.), Plenum Publishing Corp., New York, N.Y., 1986.
Wright et al., "Convenient Synthesis of 2-Halo-2'-deoxyadenosines," *J. Org. Chem.*, 52, 4617-4618 (1987).
Kazimierczuk et al., "Synthesis of 2'-Deoxytubercidin, 2'-Deoxyadenosine, and Related 2'-Deoxynucleosides via a Novel Direct Stereospecific Sodium Salt Glycosylation Procedure," *J. Am. Chem. Soc.*, 106, 6379-6382 (1984).
Montgomery, "The Chemistry and Biology of Nucleosides of Purines and Ring Analogs," in *Nucleosides, Nucleotides, and Their Biological Applications*, Academic Press, Inc., 1983, New York, N.Y., pp. 19-46.

Primary Examiner—Johnnie R. Brown
Assistant Examiner—L. Eric Crane
Attorney, Agent, or Firm—Joseph J. Brindisi

[57] ABSTRACT

This invention relates to a novel process for preparing 2-chloro-2'-deoxyadenosine (2-CdA) having the following formula

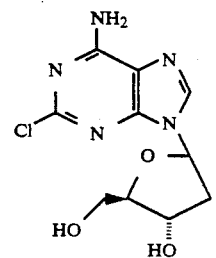

from a compound of the following formula

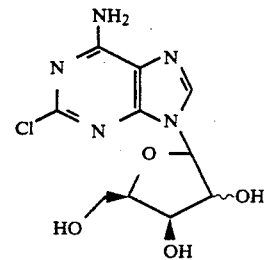

The invention also relates to intermediates which are useful in preparing 2-CdA. The compound 2-CdA is useful as an antileukemic agent, i.e., in treating leukemias, such as hairy cell leukemia.

3 Claims, No Drawings

INTERMEDIATES USEFUL IN A SYNTHESIS OF 2-CHLORO-2'-DEOXYADENOSINE

CROSS-REFERENCE TO RELATED APPLICATION

This application is a continuation-in-part of co-pending application Ser. No. 810,992, field Dec. 18, 1991, now abandoned.

I. FIELD OF THE INVENTION

This invention relates to a novel process for preparing 2-chloro-2'-deoxyadenosine (2-CdA) having the following formula

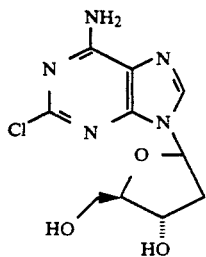

from a compound of the following formula

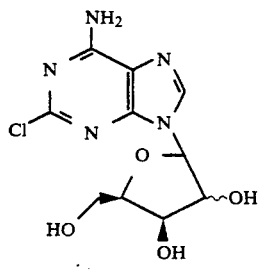

The invention also relates to novel intermediates useful in the preparation of 2-CdA.

2-CdA is useful as an antileukemic agent, i.e., in treating leukemias, such as hairy cell leukemia and L 1210 leukemia. 2-CdA is also know to have immunosuppresive activity.

II. BACKGROUND OF THE INVENTION

Processes for preparing 2-CdA are known. European Patent Application No. 173,059 A2 and R. Robins et al., J. Am. Chem. Soc., 106, 6379 (1984) disclose the preparation of 2-CdA. The preparation consists of the glycosylation of 2,6-dichloropurine with 1-chloro-2'-deoxy-3',5'-di-O-p-toluoyl-b-D-erythro -pentofuranose to yield the N-9 glycosylated purine, 2,6-dichloro-9-(2-deoxy-3,5-di-O-p-toluoyl-b-D-erythropentofuranosyl)-purine, which i subsequently reacted with ammonia to yield 2-CdA. The synthesis of 2-CdA by this process, however, has several drawbacks. First, the 2,6-dichloropurine is a costly commercial intermediate. Second, the glycosylation of the 2,6-dichloropurine yields an N-7 glycosylated side product, 2,6-dichloro-7-(2-deoxy-3,5-di-O-p-toluoyl -β-D-erythro-pentofuranosyl)purine, that has to be separated from the desired N-9 glycosylated product.

Processes are also disclosed for preparing compounds having the following formula

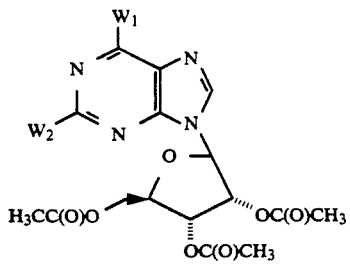

wherein $W^1$ is Cl or $NH_2$, and $W^2$ is Cl or $NH_2$, from the natural nucleoside guanosine (See, M. Robins et al., Can. J. Chem., 59, 2601 (1981); M. Robins et at., Nuc. Acids Symp. Ser., 9, 61 (1981). M. Robins et al., Can. J. Chem., 59, 2601 (1981) also disclose a process for preparing a compound of the formula

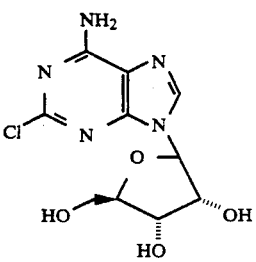

by reacting the aforesaid compound wherein $W^1$ and $W^2$ are Cl with ammonia in a protic solvent such as water or an alcohol. However, these publications do not disclose or suggest a method for effecting the 2-deoxygenation of these compounds.

In addition, processes are disclosed for effecting the 2'-deoxygenation of compounds of the following formula

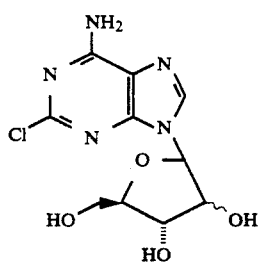

(See. M. Robins et al., J. Am., Chem. Soc., 103, 932 (1981); M. Robins et at., J. Am. Chem. Soc., 105, 4059 (1983)). These publications, however, do not disclose or suggest a process for converting a nucleoside having a halo substituent in the nucleotide moiety to their corresponding 2'-deoxygenated nucleosides. Furthermore, it is disclosed that the steps that are used to effect the deoxygenation are not applicable where the starting nucleoside has a halogenated nucleotide moiety, i.e., such a nucleoside cannot be converted to the corresponding 2-deoxygenated nucleoside due to the presence of the halo substituent. R. Robins et al., J. Am. Chem. Soc., 106, 6379 (1984); J. Montgomery, In "Nucleosides, Nucleotides, and their Biological Applications", J. Rideout, D. Henry, M. Beecham; Edgs.; Academic Press: New York, p.p. 19–46 (1983).

3

Consequently, none of the aforesaid publications disclose a process for preparing 2-CdA from a starting material other than 2,6-dichloropurine. In addition, the publications do not disclose a process for preparing 2-CdA that does not require a glycosylating reaction step or the separation of isomeric N-glycosylated products. Furthermore, there is no disclosure of the preparation of 2-CdA starting from a 2'-oxygenated nucleoside.

III. SUMMARY OF THE INVENTION

The present invention relates to a novel process for preparing 2-CdA from a compound of the following formula

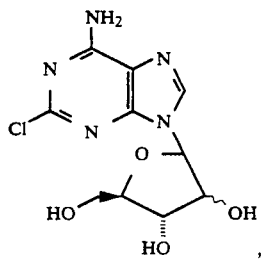

which process comprises the steps of silylating the hydroxyl groups of the compound at the 3' and 5' positions, acylating the hydroxyl group at the 2' position, deoxygenating the acylated 2' position and desilylating the hydroxyl groups at the 3' and 5' positions.

IV. DETAILED DESCRIPTION OF THE INVENTION

The invention in its broadest aspects relates to a novel process for preparing the compound 2-CdA having the following formula

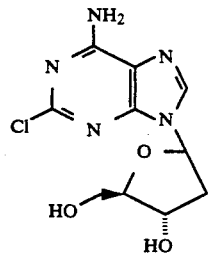

Scheme I discloses the process of the invention for preparing 2-CdA. The process employs as the starting material a 2'-oxygenated nucleoside, compound A wherein the bond at the 2 position denotes that the hydroxyl attached at that position can be down ( ), up ( ) or mixtures thereof.

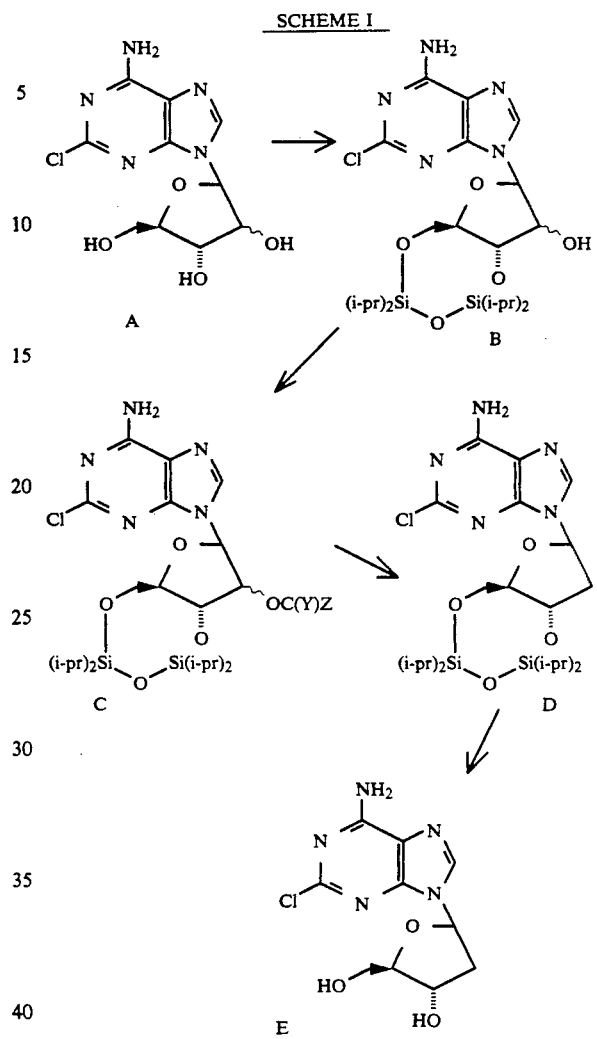

In the first step of the process, compound B is prepared by reacting compound A with a silylating agent in the presence of a base such as pyridine. The silylating agent has the formula $(i\text{-}pr)_4Si_2O(X)_2$, wherein X is a halo, such as 1,3-dichloro-1,1,3,3-tetraisopropyl disiloxane. The reaction takes from about 1 to 6 hours, at about room temperature or reflux, and the reaction is carried out under dry atmospheric conditions such as $N_2$ or argon to prevent the hydrolysis of the silylating agent.

In the second step of the process, compound C is prepared by acylating compound B with an acylating agent in the presence of an organic base such as 4-dimethylaminopyridine, or an inorganic base such as an alkali hydroxide or carbonate, e.g., $Na_2CO_3$ or KOH, in water. The acylating agent has the formula, XC(S)Z, wherein X as defined above, Z is $YR^2$ or $R^2$, Y is S or O, and $R^2$ is a $C_{1-5}$ straight- or branched-chain alkyl, phenyl or substituted phenyl where the substituents are chloro or methyl; preferably phenyl chlorothionoformate. A strong base should be employed where Z is $YR^2$. However, the reaction can be carried out under basic aqueous conditions as noted above. The reaction is carried out preferably in an organic solvent such as methylene chloride or acetonitrile under dry atmospheric conditions as described above to prevent the hydrolysis of the acylating agent. The reaction is carried out at about room temperature to 80° C., and for about 1 to 16 hours.

In the next step, compound C is reacted with an organotin hydride such a tri-n-butyltin hydride or triphenyltin hydride, and a radical initiator such as, for example, azobisisobutyronitrile, 4,4-azobis(4-cyanovaleric acid), or azobis(1-cyanocyclohexane) to yield compound D. The reaction is carried out in a solvent such as benzene or toluene, at a temperature of from about 60° C. to reflux, for about 1 to 10 hours, and the reaction is preferably carried out under dry atmospheric conditions as described above.

The last step of the process, involves desilylating compound D to yield 2-CdA (E). The desilylation is carried out under hydrolysis conditions, e.g., using an acid or a base such as dilute to 6N HCl or dilute to 6 N NaOH, in a solvent such as dioxane, water, or a straight- or branched-chain $C_{1-4}$ alcohol (methanol, isopropanol or butanol). In the alternative, the desilylation is preferably carried out in the presence of a fluoride source such as tetra-n-butylammonium fluoride, sodium fluoride or potassium fluoride, in a solvent such as tetrahydrofuran or ether, and under dry atmospheric conditions as described above. The desilylation is carried out at about room temperature to 60° C., for about 1 to 2 hours.

The present invention is further directed to the novel intermediates compounds B, C and D, as shown in Scheme I. The intermediates are useful in the production of 2-CdA.

The preparation of the starting material, compound A, from guanosine, a natural 2'-oxygenated nucleoside, or an analogue or derivative thereof is shown in Scheme II.

SCHEME II

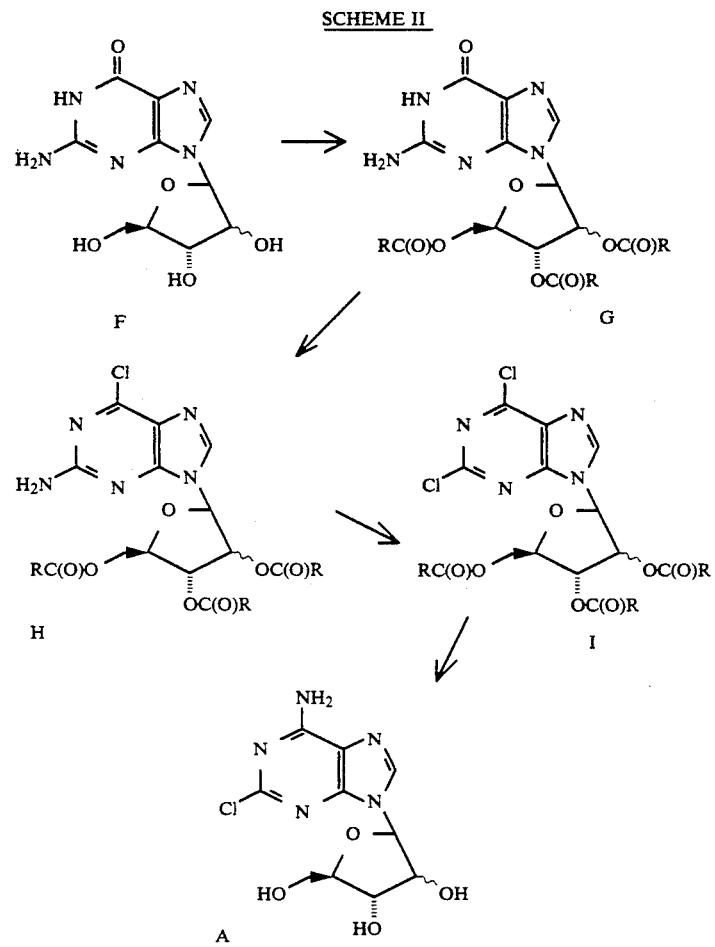

The preparation of guanosine, compound F wherein the 2'-hydroxy is down, is disclosed by P. Levine et al., Nucleic Acids, p. 163 (New York, 1931) and J. Davoll, Chem. Soc., 1593 (1958). The preparation of the analogue of guanosine, i.e., compound F wherein the 2'-hydroxy is up, is disclosed by J. Med. Chem., 25(6), 1899 (1988).

Compounds G and H, which are derivatives of compound F, are prepared essentially according to the method disclosed by M. Robins Et al., Can. J. Chem., 99, 2601 (1981). The preparation of compound G, wherein R is a $C_{1-5}$ straight- or branched-chain alkyl or phenyl, involves the acylation of compound F with an appropriate acylating agent. The preparation of compound H involves reacting compound G with an inorganic acid chloride.

Compound I is then prepared essentially according to the method disclosed by M. Robins et al., Nuc. Acids Symp. Ser., 9, 61 (1981). In this method, compound H is reacted with a nitrosylating agent, e.g., alkyl nitrite, and a chloride source, e.g., alkyl chloride or arylalkyl chloride.

Compound A is then prepared essentially as described by M. Robins et al., Can. J. Chem., 59, 2601 (1981), i.e., by reacting compound I with ammonia or ammonium hydroxide.

The compound 2-CdA is useful as an antileukemic agent, i.e., in treating leukemias, such as hairy cell leukemia and L1210 leukemia. 2-CdA is also known to have immunosuppressive activity. See, D. Carson et al., *Proc. Natl. Acad. Sci. USA*, 81, 2232 (1984).

The following examples describe the invention in greater particularity and are intended to be a way of illustrating but not limiting the invention.

V EXAMPLES

Example 1

Preparation of 2',3',5'-O-triacetyl guanosine

A mixture of guanosine (355 g, 1.25 M), acetic anhydride (0.750 L), pyridine (0.375 L) and dimethylformamide (1 L) is stirred at room temperature for 2 hours and then heated at 75° C. for 4 hours. After the heating, the mixture is cooled to room temperature and stirred overnight Most of the solvent is then removed by vacuum distillation at 45° C. to yield a white precipitate. The solid is isolated by filtration and washed with isopropanol. The solid is suspended in isopropanol, and heated to reflux whereupon most of the solid dissolves. The isopropanol is then allowed to cool to room temperature, and filtered to yield a white solid that is dried overnight in a vacuum oven at 60° C. to yield the title compound (358 g, 69.8%).

Example 2

Preparation of 9-(2',3',5'-O-triacetyl-b-D-ribofuranosyl)-2-amino-6-chloropurine A mixture of the compound of Example 1 (480 g, 1.17 M), N,N-dimethylaniline (150 mL), tetraethylammonium chloride (386.4 g) and acetonitrile (0.70 L) is prepared, and then phosphorous oxychloride (400 mL) is added slowly (dropwise) over 3 hours at room temperature under a $N_2$ atmosphere. After the addition, the mixture is heated at 100° C. for 14 minutes, and then cooled to room temperature. Most of the solvent is removed in vacuo to yield a red oil. The oil is treated with methylene chloride ($CH_2Cl_2$)(2 L), and then poured into ice water (1.5 L). The organic layer is separated and the aqueous layer extracted with $CH_2 Cl_2$ (3×500 mL). The separated organic layer and the organic extracts are combined, washed with a saturated sodium bicarbonate solution until a pH of 6 to 7 is reached, and then washed with ice-water (2 ×1 L). The organic layer is dried over sodium sulfate, and the solvent removed in vacuo to yield a thick oil. The oil is treated with isopropanol (200 mL), stirred at 45° C. for 1 hour, allowed to cool to room temperature, and left overnight whereupon a precipitate is formed. The precipitate is isolated by filtering and then the precipitate is washed with cold isopropanol to yield the title compound (235 g, 47%).

Example 3

Preparation of 9-(2',3',5'-O-triacetyl-b-D-ribofuranosyl)-2,6-dichloropurine n-Pentyl nitrite (98 g, 838 mM) is added over one hour at room temperature under nitrogen to a mixture of the compound of Example 2 (350 g, 819 mM), triphenylmethyl chloride (500 g, 1.79 M) and potassium carbonate (65 g) in $CH_2Cl_2$ (3 L). The resulting mixture is heated at reflux for 20 minutes, cooled to room temperature and filtered. The filtrate is concentrated in vacuo, and the resulting residue is purified by column chromatography on silica gel (2.5 kg, ethyl acetate/hexane 1:4–3:7) to yield the title compound as a pale yellow solid (272 g, 74%).

Example 4

Preparation of 2-chloroadenosine

A mixture of the compound of Example 3 (271 g, 606 M), concentrated ammonium hydroxide (4 L) and tetrahydrofuran (0.5 L) is stirred at room temperature under nitrogen for 4 days. The solvent volume is reduced in vacuo and the resulting residue is triturated with absolute ethanol. The title compound is precipitated out of the ethanolic solvent to yield a light brown solid, (159 g, 87%).

Example 5

Preparation of 2-chloro-(3',5'-O-tetraisopropyldisiloxyl)adenosine

A mixture of the compound of Example 4 (13 g, 43 mM), 1,3-dichloro-1,1,3,3-tetraisopropyldisiloxane (15 g, 47.6 mM) and pyridine (150 mL) is stirred at room temperature under nitrogen for 3 hours. The solvent volume is reduced in vacuo and the resulting residue is dissolved in $CH_2Cl_2$ (250 mL), washed with a saturated copper sulfate solution (2×150 mL) and dried with sodium sulfate. The organic layer is concentrated in vacuo and purified by column chromatography on silica gel (200 g) with ethyl acetate/hexane (1:1) to yield the title compound as a white powder (14.7 g, 63%, mp 198-200° C.); $^1$H-NMR (CDCl$_3$):δ7.9 (s, 1H, C$_8$H), 6.32 (bs, 2H, NH$_2$), 5.89 (s, 1H, C$_1$·H); IR(KBr):3400, 1650, 1595, 1040 cm$^{-1}$.

Anal. Calcd. for $C_{22}H_{38}ClN_5O_5Si_2$: C, 48.55; H, 7.04;N, 12.87.

Found: C, 48.66; H, 6.81;N, 12.71.

Example 6

Preparation of 2-chloro-2'-O-phenoxythiocarbonyl-(3',5'-O-tetraisopropyldisiloxyl)adenosine Phenyl chlorothionoformate (4.66 g, 27 mM) is added to a mixture of the compound of Example 5 (14 g, 25.8 mM), 4-dimethylaminopyridine (DMAP) (6.88 g, 56.4 mM) and acetonitrile (400 mL) at room temperature under nitrogen, and stirred overnight. The solvent is removed in vacuo and the residue is purified by column chromatography on silica gel (200 g) with ethyl acetate/hexane (4:6) to yield the title compound as a pale yellow powder (9.8 g, 56%, mp 153-155° C.); $^1$H-NMR (CDCl$_3$):δ7.9 (s, 1H, C$_8$H), 7.1~7.5 (m, 5H, aromatic protons); IR(KBr):1640, 1590, 1200 cm$^{-1}$.

Anal. Calcd. for $C_{29}H_{42}ClN_5O_6SSi_2$: C, 51.19; H, 6.22;N, 10.29.

Found: C, 51.11; H, 6.50;N, 19.21.

Example 7

Preparation of 2-chloro-2'-deoxy-(3',5'-O-tetraisopropyldisiloxyl)adenosine

A mixture of the compound of Example 6(5.8 g, 8.54 mM), tri-n-butyltin hydride (3 mL, 11 mM) and azobisisobutyronitrile (320 mg) in benzene (100 mL) is heated to reflux for 3 hours under nitrogen. After cooling, the solvent is removed in vacuo and the residue is purified by column chromatography on silica gel (200 g) with ethyl acetate/hexane (4.5:5.5) to yield the title compound as a white powder (3.78 g, 84%, mp 171–173° C)

$^1$H-NMR (CDCl$_3$):δ7.95 (s, 1H, C$_8$H), 6.43 (bs, 2H, NH2); IR(KBr): 3350, 3180, 1660, 1597, 1310 cm$^{-1}$.

Anal. Calcd. for C$_{22}$H$_{38}$ClN$_5$O$_4$Si$_2$: C, 50.02; H, 7.25;N, 13.26.

Found: C, 50.41; H, 7.41;N, 12.85.

Example 8

Preparation of 2-chloro-2'-deoxy-adenosine

A mixture of the compound of Example 7 (2.5 g, 4.74 mM), and tetra-n-butylammonium fluoride in tetrahydrofuran (1.1 M, 8.6 mL, 9.46 mM) in tetrahydrofuran (10 mL) is stirred at room temperature under nitrogen for 2 hours. The solvent volume is reduced in vacuo and the resulting residue is treated with water (200 mL) and extracted with ether (3×20 mL). The aqueous layer is purified by preparative HPLC (C-18 reverse phase column, methanol/water 15:85 to 20:80) to yield the title compound (600 mg, 44%, mp>230° C.).

What is claimed is:

1. A compound of the following formula

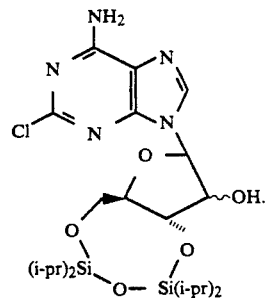

2. A compound of the following formula

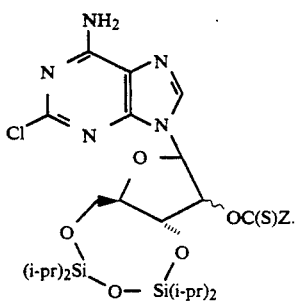

wherein Z is R$^2$ or YR$^2$; Y is O or S; and R$^2$ is a C$_{1-5}$ straight- or branched-chain alkyl or phenyl.

3. A compound of the following formula

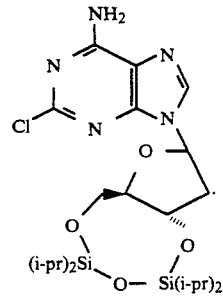

* * * * *